United States Patent [19]

Levi et al.

[11] Patent Number: 5,583,776

[45] Date of Patent: Dec. 10, 1996

[54] DEAD RECKONING NAVIGATIONAL SYSTEM USING ACCELEROMETER TO MEASURE FOOT IMPACTS

[75] Inventors: Robert W. Levi, Anaheim; Thomas Judd, Fountain Valley, both of Calif.

[73] Assignee: Point Research Corporation, Santa Ana, Calif.

[21] Appl. No.: 405,087

[22] Filed: Mar. 16, 1995

[51] Int. Cl.⁶ ................................................. G01C 22/00
[52] U.S. Cl. ..................... 364/450; 364/443; 364/460
[58] Field of Search ................................. 364/449, 450, 364/452, 460, 454, 443; 235/105; 340/944; 73/490

[56] References Cited

U.S. PATENT DOCUMENTS

| | | | |
|---|---|---|---|
| 3,635,399 | 1/1972 | Dahlquist et al. | 235/105 |
| 3,797,010 | 3/1974 | Adler et al. | 340/323 |
| 3,901,086 | 8/1975 | Griffiths et al. | 73/490 |
| 4,053,755 | 10/1977 | Sherrill | 364/561 |
| 4,149,417 | 4/1979 | Griffiths et al. | 73/490 |
| 4,409,992 | 10/1983 | Sidorenko et al. | 128/782 |
| 4,991,126 | 2/1991 | Reiter | 364/561 |
| 5,117,301 | 5/1992 | Tsumura | 359/154 |
| 5,117,444 | 5/1992 | Sutton et al. | 377/24.2 |
| 5,367,458 | 11/1994 | Roberts et al. | 364/424.02 |
| 5,485,402 | 1/1996 | Smith et al. | 354/566 |

OTHER PUBLICATIONS

Meijer, et al., *Methods to Assess Physical Activity with Special Reference to Motion Sensors and Accelerometers*, IEEE Transactions on Biomedical Engineering, Mar. 1991, vol. 38, No. 3, pp. 221–229.

"American Practical Navigator", originally by N. Bowditch, LL.D., 1966—Corrected Print, published by the U.S. Navy Hydrographic Office.

*Primary Examiner*—Michael Zanelli
*Attorney, Agent, or Firm*—Price, Gess & Ubell

[57] ABSTRACT

A microcomputer-assisted position finding system that integrates GPS data, dead reckoning sensors, and digital maps into a low-cost, self-contained navigation instrument is disclosed. A built-in radio frequency transponder allows individual positions to be monitored by a central coordinating facility. Unique dead reckoning sensors and features are disclosed for ground speed/distance measurement and computer-aided position fixes.

15 Claims, 8 Drawing Sheets

DEAD RECKONING NAVIGATIONAL SYSTEM USING ACCELEROMETER TO MEASURE FOOT IMPACTS

BACKGROUND OF THE INVENTION

1. Field of the Invention

The present invention relates generally to navigational systems and, in particular, to electronic, portable navigational systems that use radionavigational data and dead reckoning for foot navigation.

2. Description of Related Art

The term "dead reckoning" (DR) refers to a position solution that is obtained by measuring or deducing displacements from a known starting point in accordance with motion of the user. Two types of DR are known: inertial navigation and compass/speedometer.

Inertial Navigation Systems (INS) use data from three orthogonal accelerometers. Double integration calculates position from acceleration as the user moves. Three gyros are also required to measure the attitude of the accelerometers and remove the effects of gravity. Results of the integration are added to the starting position to obtain current location. The need for six accurate and stable sensors makes the cost of INS high.

INS position errors increase with the square of time due to the double integration. These errors could easily be a large fraction of a foot traveler's ground speed. A typical INS system has a drift rate on the order of 0.8 miles per hour (mph). Although this error could easily exceed the rate of travel for a person walking on foot, it may be negligible for a jet aircraft. Future developments in inertial sensors may lower costs, but improvements in accuracy are less predictable. For these reasons, inertial navigation may not be a viable option for low-cost foot traveler navigation.

Regarding compass/speedometer DR systems, a compass and a speed/distance sensor is a direct means to determine location, and has been automated with microcomputers in vehicular applications. Simple and low-cost DR systems for land navigation have often been built using only a compass and a ground speed sensor for measurements.

Generally, these systems have been designed for automobiles or trucks, with the speed sensor output being derived from rotation of the road wheels. Strap-down inertial navigation systems have become popular due to the numerical processing capability of microprocessors and are lower cost and power than stable platform inertial systems.

A considerable amount of work has been done related to the integration of a Global Positioning System (GPS) and INS. The importance of supplementing the GPS position solution with an integrated GPS/DR system is evidenced by the considerable work that has been done in this area. Work has not been done specifically for foot traveler, hiker, or pedestrian use in this area.

SUMMARY OF THE INVENTION

GPS data can be either unreliable or unavailable due to antenna shading, jamming, or interference. The present invention discloses incorporation of DR functions with GPS position information, thus providing the individual foot traveler with an autonomous navigation capability. The present invention discloses a microcomputer-assisted position finding system that integrates GPS data, DR sensors, and digital maps into a low-cost, self-contained navigation instrument. A built-in radio frequency transponder allows individual positions to be monitored by a central coordinating facility. Unique DR sensors and features are disclosed for ground speed/distance measurement and computer-aided position fixes.

The navigation system of the present invention combines a digital electronic compass with both a silicon pedometer and a barometric altimeter to generate a low-cost, computerized DR system. These sensors are used in a complementary configuration with GPS and digital electronic maps. Compared with a stand-alone GPS receiver, the integrated GPS-DR navigation system of the present invention provides advantages during GPS outages. In these outages, DR continuously tracks the user's position without references to external aids or signals.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically.

The present invention analyzes the frequency of a user's footsteps to aid in the detection of future footsteps, and further to aid in determining the size of footsteps taken by the user. The present invention also incorporates several directional calibrating and position-fixing algorithms which are used in combination with digital maps.

A. Use of Frequency to Detect Steps and Determine Step Size

The present invention for a ground speed/distance sensor is an improvement over a common hiker's pedometer. Existing electronic pedometer designs use a spring-loaded mechanical pendulum to sense walking motions of the user. The pendulum operates a simple switch so that the up-down motion of the pendulum may be counted by the unit's electronics. A scale factor that is proportional to the user's stride length is applied to the count. The assumption is that each count represents one step, however due to the pendulum dynamics extra bounces can occur. Sensitivity and bouncing depends on the spring rate and the pendulous mass. Multiplying step counts by the scale factor yields a measure of distance. Prior-art pedometers require manual calibration, are unreliable, and cannot be interfaced to a computer.

The present invention uses an accelerometer to provide acceleration data indicative of footsteps. The basic sensor for the navigation pedometer of the presently preferred embodiment comprises a silicon accelerometer. The accelerometer may be mounted or attached at any convenient point on the user's body, as long as it can sense the harmonic motions and impact accelerations that result from walking or running. Other footstep sensors may be used, such as force sensors embedded in the user's shoe. Shoe sensors, however, may be impractical, since they require special shoe modifications and possibly wires up the leg of the user. Silicon accelerometers have recently become available at low cost from several vendors. The device is "micromachined" from solid silicon using much the same techniques as used for integrated circuit manufacture.

The sensing element of the presently preferred embodiment comprises a mass suspended on a flexure. When the mass is subjected to an acceleration force (for example, during a footstep), the resulting motion can be detected by an electrical resistance change in the flexure or by motion measurement of the mass. The resonant frequency of the accelerometer is much higher than ordinary electromechanical pedometers. Similar sensors are used for crash detection in automotive air bag systems. The sensed footsteps are converted to distance and velocity.

Figure 1:
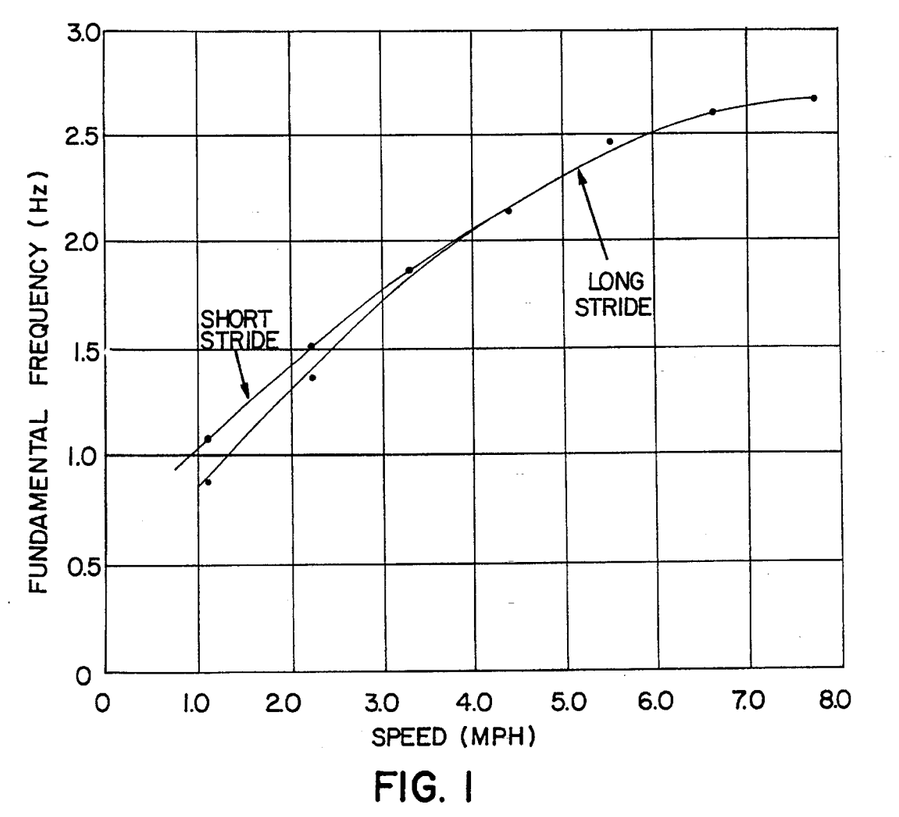
FIG. 1 illustrates a pedometer calibration curve of speed versus fundamental frequency for two different users.

Lab experiments were conducted using the accelerometer footstep sensor of the present invention on a treadmill. FIG. 1 shows the acceleration data resulting from walking at a speed of 3.3 mph on the treadmill. This data indicates that simple pulse counting is unreliable for counting the acceleration peaks that correspond to footsteps. The character of the data changes substantially as speed changes. Simple pulse counting is the method used by existing pedometers.

The present invention combats problems associated with simple pulse counting by extracting the fundamental frequency of a hiker's footsteps, using digital signal processing techniques. More complex peak counting algorithms are also feasible.

A Fast Fourier Transform (FFT) spectrum analyzer is used in conjunction with treadmill testing to gather fundamental-frequency data from 1 to 7 mph, for example. Thus, a fundamental frequency is determined for each speed of a hiker, by collecting acceleration peaks corresponding to the user's footsteps at that speed, taking an FFT of the data, and recording the fundamental frequency for the hiker at that speed.

Figure 2:
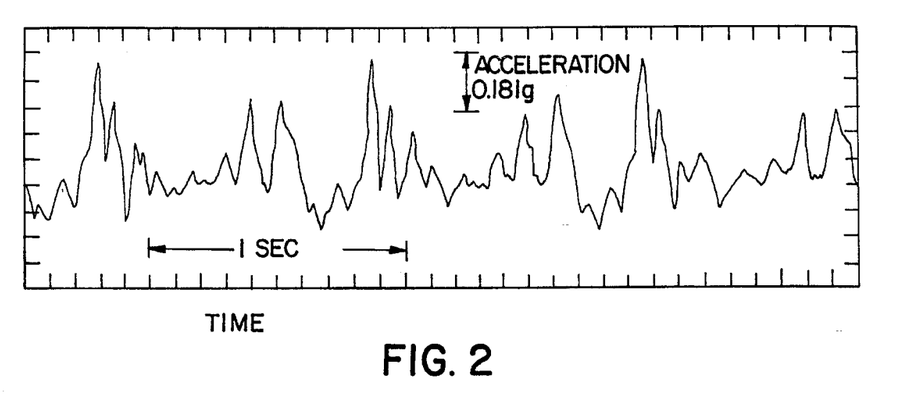
FIG. 2 illustrates raw data from a silicon accelerometer plotted on a time axis.

A typical spectrum is shown in FIG. 2. This spectrum corresponds to a hiker's acceleration peaks at 3.3 mph. FIG. 2 shows that the fundamental frequency is about 1.8 Hz for the hiker's speed of 3.3 mph. The present invention thus collects fundamental frequencies for a user at various speeds. From this data, Applicants have discovered that the fundamental frequency is indeed proportional to a user's speed.

Figure 3:
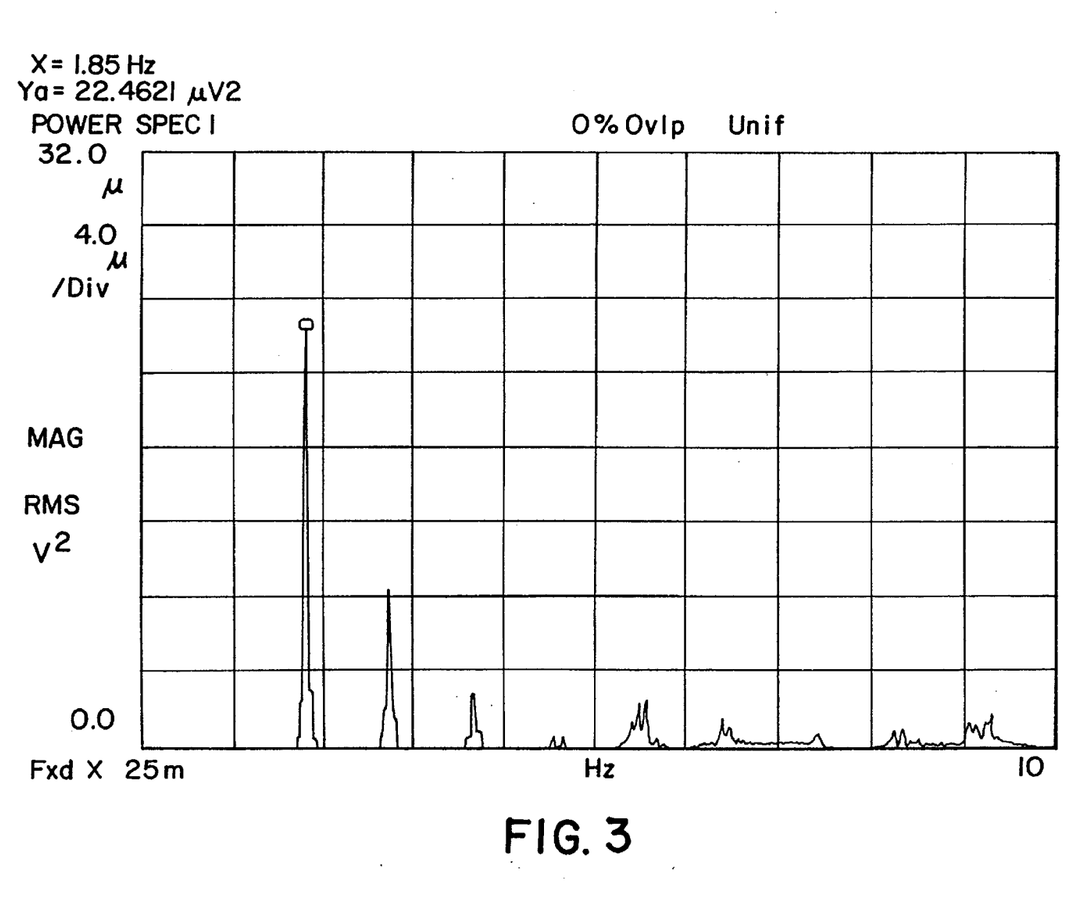
FIG. 3 illustrates a frequency domain representation of the silicon accelerometer raw data of FIG. 2.

FIG. 3 shows a calibration curve resulting from a plot of the fundamental frequencies derived via FFT and the treadmill speed. The linearity of the results is a good indication that this method works without a large amount of complex mathematical manipulations. Two curves are shown in FIG. 3. One of the curves is for a person with a relatively short stride, and the other curve is for a person with a longer stride. As expected, the person with the shorter stride must "walk faster," which results in higher fundamental frequencies for the same speed for that person with the shorter stride. This corresponds to step size increasing with increasing speed. The tapering off at the higher speeds indicates that step size is increasing.

In a fielded system, automatic calibration using GPS velocity can be used with a military GPS or Differential GPS receiver to obtain a calibration curve fit to the user's stride and terrain traveled. With a civilian GPS receiver and selective availability velocity accuracies of about 1 m/s are not good enough for velocity calibration.

Walking thus produces a periodic variation in vertical acceleration, which is measured on the user's body and indicated by the accelerometer. Peaks in the acceleration correspond to individual steps. The fundamental period of the data is the step frequency for that speed. Hence, two independent methods may be used by the present invention to determine displacement: one based on the detection of single steps, and another based on the determination of the frequency content of the signal from a number of steps. These two methods may be used separately or in combination.

1. Peak Detection Algorithm

Figure 4:
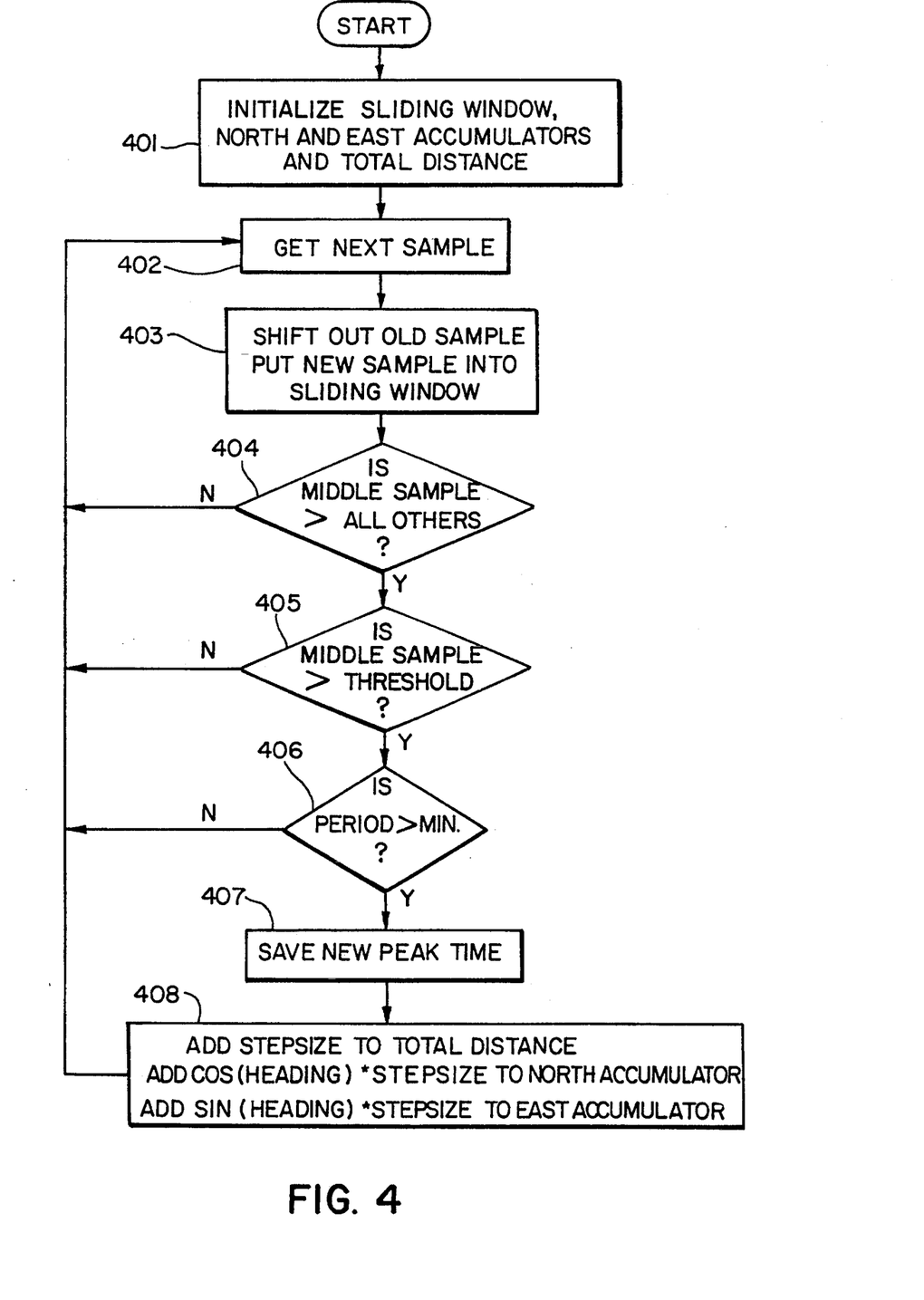
FIG. 4 illustrates a flow chart for peak detection according to the presently preferred embodiment.

Peak or step detection allows determination of distance directly by a scale factor. A sliding window of the data is maintained with an odd number of samples. Using an odd number of samples ensures that there is always a central sample. The central sample in the window is tested. Refer to FIG. 4.

Step 401: First, the sliding window is set to zero, as are North and East distance accumulators, and the total distance traveled.

Step 402: The next accelerometer sample is taken.

Step 403: The samples in the sliding window are shifted, the oldest falls off the far end, the new sample is placed in the near end.

Step 404: The middle sample is compared to all the others. If it is greater than the rest, then there is a potential step or peak in the data. If not, another sample is taken.

Step 405: The magnitude of the peak must be above a minimum threshold to prevent false detection on small fluctuations that could not have been caused by footfalls. If the magnitude of the peak is below the threshold, another sample is taken.

Step 406: The time since the last peak must be greater than some minimum period. If it is expected that steps will occur no more often than three times per second, for example, then peaks that are closer in time than ⅓-second are not allowed. If the period is too small, another sample is taken.

Step 407: A peak exists. The time is marked so it may be used for comparison in Step 6 the next time around.

Step 408: Total distance traveled is

*New distance=old distance+step size*

The north and east accumulators are modified as follows:

*New North=Old North+step size * cosine (heading)*

*New East=Old East+step size * sine (heading)*

The average or steady-state value of the data is subtracted from the accelerometer samples to remove gravity effects. The resulting dynamic component of the data contains the useful peak information. The dynamic data is filtered to attenuate accelerations that are outside the known frequency band of human movement. Measurements have shown that the fundamental frequencies for normal human walking and running are below 10 Hz. A peak is noted if the data sample is the largest value in a set of samples that include times before and after the peak sample. It also must be larger than a minimum threshold value, and must not occur within a set time period, measured from the previously detected peak. The user's stride length is added incrementally to the accumulated distance every time a peak is detected. North and East components of the stride are calculated using data from the direction sensor. The component displacements are added to separate North and East accumulators, and are used to calculate the total displacement from the starting point.

2. Frequency Measurement Algorithm

Figure 5:
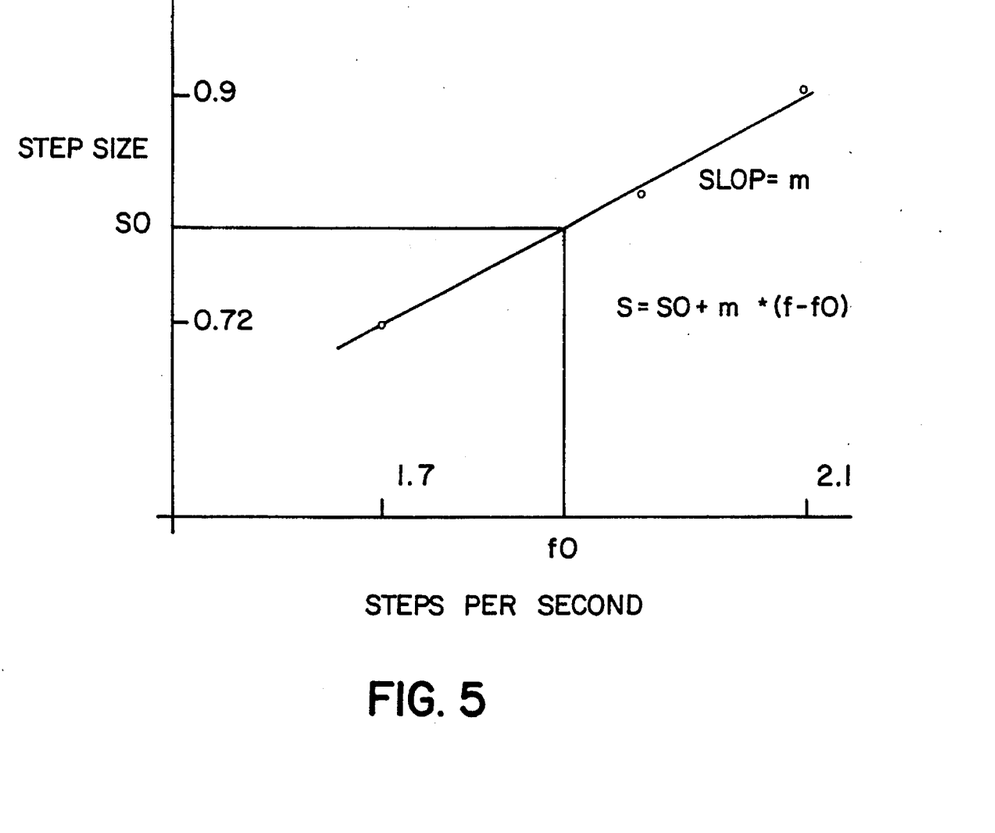
FIG. 5 illustrates the relationship between frequency of a user's steps and step size.

Frequency measurement is performed in the presently preferred embodiment primarily to obtain step size. Step size is related to frequency as shown in FIG. 5. Frequency detection relies on a Fast Fourier Transform (FFT) to estimate the frequency content of the signal, and an FFT requires that a fixed number of samples be stored prior to analysis. An FFT cannot be performed on a single sample. To keep the update rate reasonable, a sliding window of samples is used, and the FFT is recalculated after a percentage of fresh samples have been added. Refer to flow chart FIG. 6.

Figure 6:
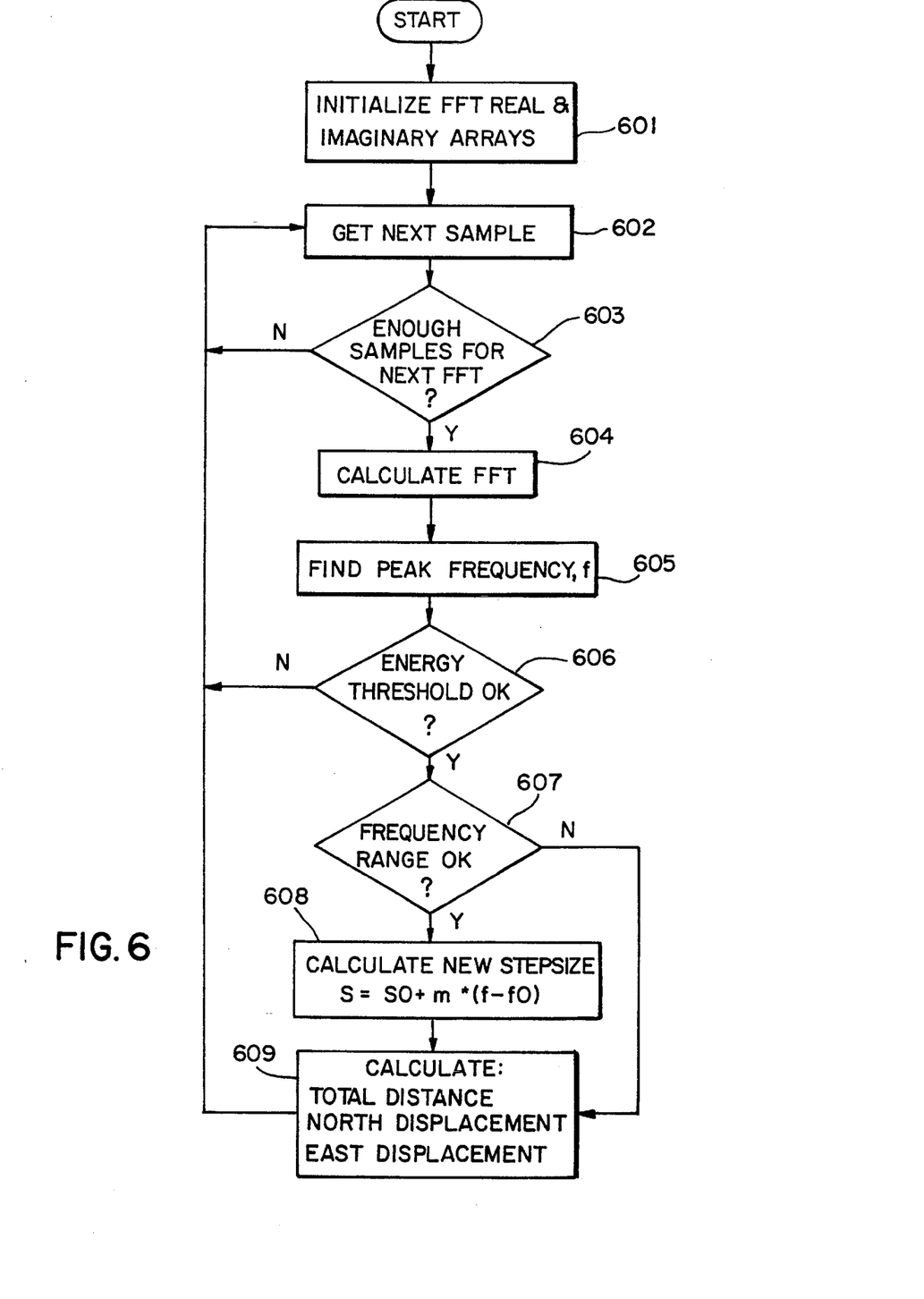
FIG. 6 illustrates the frequency measurement algorithm of the presently preferred embodiment.

Step 601: First, initialize the real and imaginary arrays to zero.

Step 602: Get the next sample and place it in the real array.

Step 603: If there are sufficient samples to perform the FFT then go on; otherwise go get the next sample. There may be a 512-point FFT, but recalculation every 128 samples may be advantageous. So if only 128 samples are new, go on.

Step 604: Calculate the FFT.

Step 605: The magnitude of each frequency bin is calculated, and the largest of these is identified as the step frequency.

Step 606: As in the peak detection algorithm, minimum limits are put on the strength of the signal, so that calculations on noise are not performed. If a minimum threshold on the signal is not met, then do not proceed to update the accumulators; rather, return to get more data.

Step 607: The range of acceptable frequencies is also limited. If they are outside normal walking frequencies (0.5 to 3.0 Hz) then proceed with the calculation but do not update the step size.

Step 608: If the frequency range check is passed, then the step size is readjusted according to the newly-calculated frequency:

*S=S0+m*(f−f0)*

Step 609: Calculation of Total Displacement and the North and East components is similar to that in the Peak Detection Algorithm, except now it is being done on multiple steps over a fixed time period. The individual components are scaled by the time period and the step frequency. For example:

North change=step size* cos (heading) * fftPeriod * f.

The fftPeriod is the time it took to collect just the new points, not the whole ensemble. Using the example above, it would be 128 sample points, not 512.

3. Dynamic Step Size Algorithm

As a user walks faster, both the step size and the frequency of steps increases. This can be simply modeled as a linear fit to observed data at different walking speeds. Looking at the calibration data shown in FIG. 5, as the number of steps increases from 1.7 to 2.1 steps per second, for example, the step size increases from 0.72 meters (2.36 feet) to 0.90 meters (2.95 feet). In this example, the frequencies span rates from a stroll to a fast walk. The step size varies by more than 20% under these conditions.

Since step size directly affects the estimated DR distance, the presently preferred embodiment adjusts step size according to the step frequency. A dynamic scaling algorithm to improve the accuracy of distance measurements of a human footstep sensor by adjusting the scale factor as a function of step frequency is thus harnessed by the present invention. Refer to flow chart FIG. 7.

Figure 7:
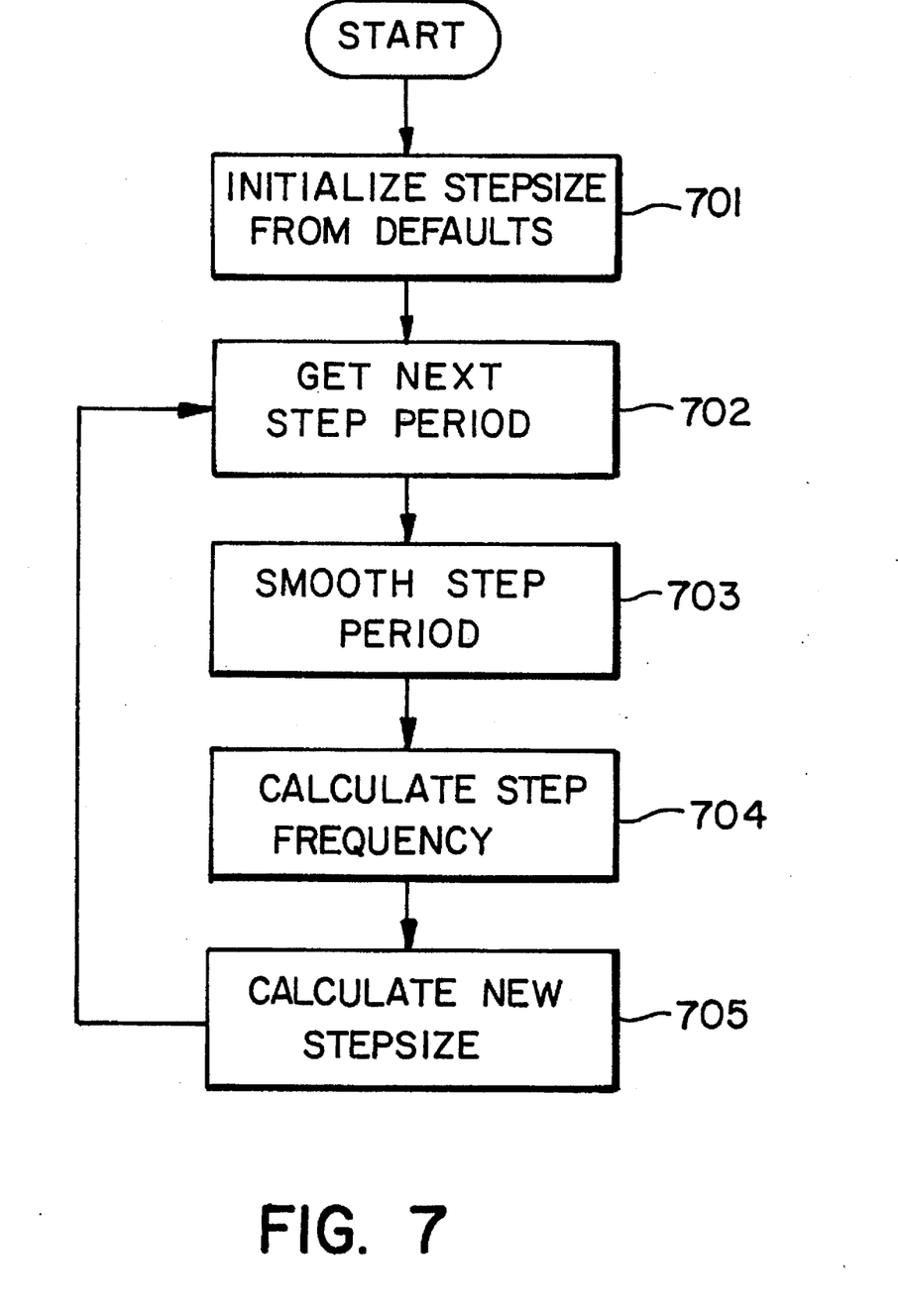
FIG. 7 illustrates the dynamic step size algorithm of the presently preferred embodiment.

Step 701: The step size may be initialized from default values stored in a configuration file. The configuration is particular to the individual person using the system and is generated during the calibration process. Three constants are saved: S0, f0, and m. S0 is the default step size, f0 is the frequency at which there is no correction to S0, and m is the slope of the calibration curve.

Step 702: The time of each step is noted as the pedometer collects data. The step period is calculated as the time between two successive steps.

Step 703: The step period is smoothed over a suitable time period. An average of the last five to ten steps is suitable.

Step 704: The step frequency is the reciprocal of the averaged step period:

*f=1/(step period)*

Step 705: The new step size is calculated by:

*S=S0+m * (f−f0)*

B. Directional Correcting and Position Fixing Algorithms Incorporating Digitized Maps DR errors depend on a number of factors, including the speed of travel and the time between position fixes. If GPS is used to update DR positions, the error depends on the duration of the GPS outage. Vehicular DR systems have achieved errors of 2% to 5% of distance traveled. According to the present invention, calculations were performed to determine errors as a percent of distance traveled using known error sources. An azimuth error of 1 degree due to the electronic compass will produce a position error of about 2% of distance traveled. In vehicular DR systems, the compass has been shown to be the predominant source of error. Hardware testing by the Applicants with actual hiking sensors showed position errors on the order of 1–2% of the distance traveled.

In view of the above problems recognized by the present invention, calibration algorithms for the compass and speed/ distance sensor are incorporated for successful implementation of the DR system. The present invention utilizes novel algorithms for accurately aligning the compass direction readout with the direction of travel of the user.

According to the present invention, combining positioning functions with digital electronic maps frees the user from the tedious and error-prone process of transferring coordinates from a digital GPS position display to a paper map. Additional benefits are realized by combining manual azimuths obtained from sightings with digital map data. The present invention's use of digital maps thus allows for accurate calibration of the DR navigation system.

To take advantage of the positioning capabilities of DR and GPS, navigation features are included in the present invention. These features are intended to help the user find his destination, identify landmarks, travel a defined route, and fix his position. Area navigation functions require calculation for determining such parameters as required course, speed, and distance, time, or velocity. These calculations are based on plane or spherical trigonometry. A capability for defining waypoints and routes comprised of connected waypoints is provided. Coordinate transformations between Latitude/Longitude and Universal Transverse Mercator (UTM) are also included.

Algorithms for exploiting the built-in digital compass and map of the presently preferred embodiment are included. Computer-aided manual fixes are automatically calculated and plotted on the map when compass azimuths on two known landmarks are available. Another technique known as a running-fix allows position determination by azimuths on a single known landmark. By taking successive azimuths on the same feature, but separated in time and distance, one of the azimuths can be advanced or retarded to coincide in time with the other bearing, thus providing data for a position fix.

The user's keypad and graphical display of the presently preferred embodiment is contained in a hand-held enclosure. Placing the compass in the hand-held enclosure allows manual sightings for bearings and manual fixes. A holster attached to the user's belt and placed near the hip holds the hand-held enclosure while the user is traveling. The hip holster location also provides an ideal mounting point for the pedometer. The keypad layout and the associated software allows the user to exercise the various functions. Features are accessed via menu-driven mode selections. The user can select the desired primary function or mode by pressing a key on the keypad. In the presently preferred embodiment, mode keys group the major functions as follows:

| | |
|---|---|
| POS | Show current position on map. Indicator shows whether the position is derived from GPS or DR. |
| GPS | Directly access the GPS receiver functions and data output. Controls for 2D/3D mode, signal/noise mask, DOP switching levels. Display of receiver status and almanac data. |
| DR | Access position solution from DR system. Graphical compass output display. Pedometer speed readout and distance since last fix. Altimeter readout. Manual and automatic calibration modes. |
| MAP | Display map data independent of current position. Show user defined features. Pan, zoom functions. |
| NAV | Area navigation, range and bearing to features. Control display of track and route. |
| WPT | Create and modify waypoints, routes and user defined features. |
| COM | Control the digital data link and transmit user's position. Review incoming and outgoing messages. Send predefined messages. |
| TIM | Timer functions such as elapsed time, estimated time of arrival. |
| ALR | Alarm functions to activate an alert when approaching a destination or preset time. |

The DR software module of the present invention performs dead reckoning (DR) navigation by sampling vector velocities for incremental course changes. Calculations can be performed continuously whenever there is a detected velocity. The DR software accesses the compass, altimeter, pedometer frequency, and calibration table data to obtain velocity magnitude and 3-D direction. The DR software normally uses GPS to obtain starting positions when GPS is valid, but also accepts manual position fixes by map selection or text entry. When GPS is not valid, DR uses the last fix, whether GPS or manual, for a start point. DR navigation is automatically used by the navigation module when GPS is unavailable. The map and navigation modules are used to select a manual fix location from the map, or to manually switch between DR and GPS navigation.

The navigation software module performs area navigation functions, and determines relative positions between locations. Calculations for required course, speed, time, and distance required are based on plane or spherical geometry. Terrain and other features selected by the user are treated as inputs to the navigation module. The navigation module may perform switching between DR and GPS navigation automatically, as conditions dictate.

In the presently preferred embodiment, GPS and DR sources are selected with a switch scheme depending on whether GPS is available. When GPS fixes are available, the DR system is continuously updated using the GPS fix. The output composite position/velocity track is displayed on the map.

Current course and speed calculation is continuously displayed on the map, along with a position track. The user can enter or select locations for area navigation. The user can determine course and range between two locations, using trigonometry algorithms. Horizontal, vertical, and slant range are found with trigonometry. The user can select a destination such as a feature or waypoint to obtain navigation information. The starting location can be current position or some other user-defined position. Time and velocity may be calculated from the given positions or course and range, such as required velocity or estimated-time-of-arrival.

The simplest method for a manual fix is to enter a known current location. The user may also take bearings with the hand-held-enclosure compass/trigger switch and automatically triangulate to establish a position fix and DR starting location.

1. DR Position Fix Algorithm

Since DR calculates an incremental change in position from a known starting point, subsequent positioning depends on accurately identifying the starting position. Periodic reinitialization of DR position is thus performed in the presently preferred embodiment, to thereby avoid accumulation of errors. These methods are independent from radionavigation aids such as GPS. Refer to flow chart FIG. 8.

Figure 8:
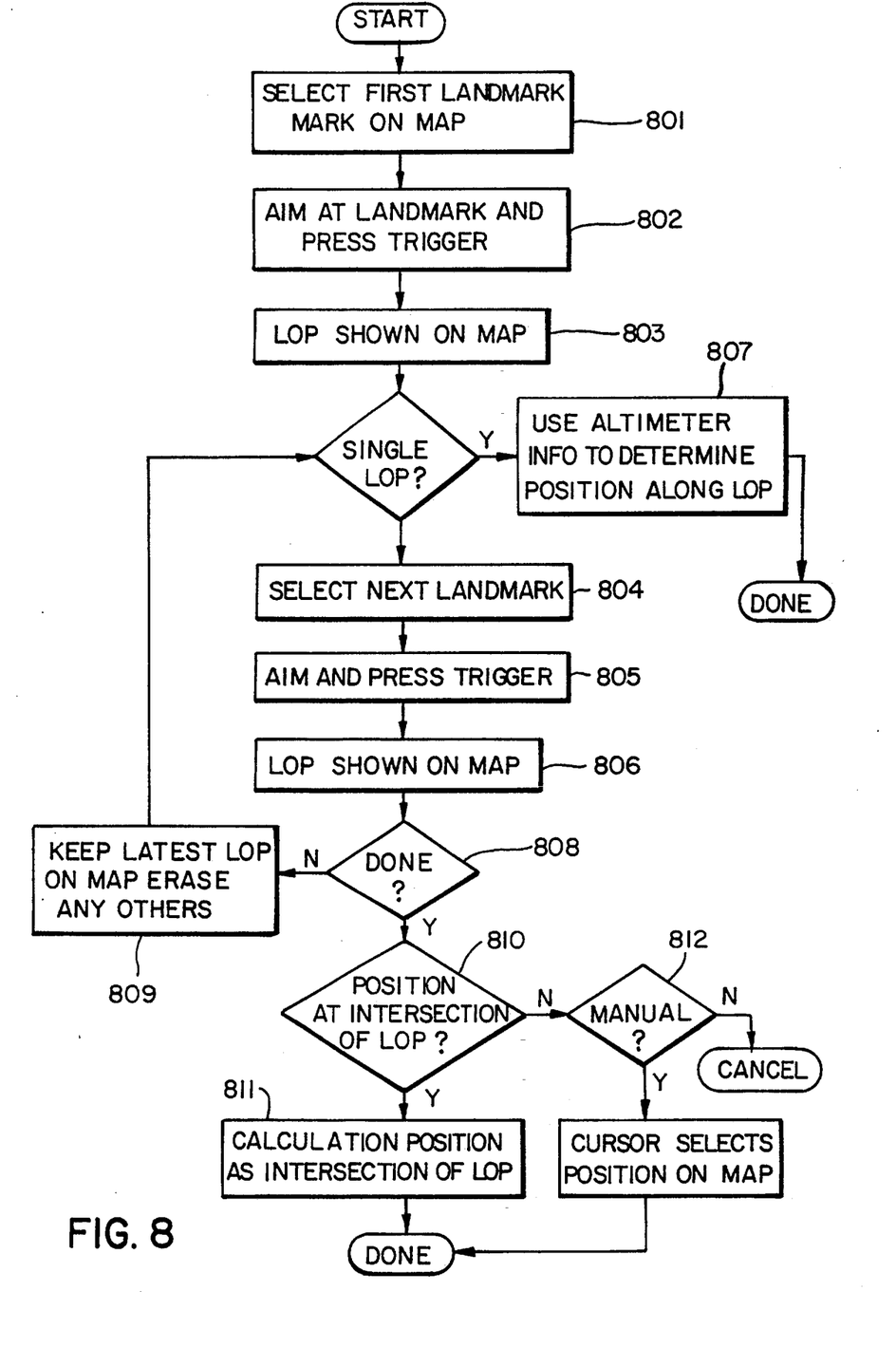
FIG. 8 illustrates a flow chart for the dead reckoning position fix algorithm of the presently preferred embodiment.

Step 801: The user visually identifies the first landmark desired for use in the manual fix. He or she then moves the electronic cursor on the digital map and marks it as his first point of reference.

Step 802: The user aims the hand-held enclosure containing the electronic compass and a sighting post at the landmark and presses a trigger switch to indicate to the computer to save that compass bearing and to associate it with the identified landmark.

Step 803: A Line of Position (LOP) appears on the map that indicates the bearing direction line from the user's position to the designated landmark. The user's actual position lies somewhere along the line.

Step 804: A second landmark is selected and Steps 802 and 803 are repeated at Steps 805 and 806. The intersection of the two LOPs indicates the user's actual position.

Step 807: If the map contains altitude contour lines, the altimeter readout may be used to locate the actual position along a single line by noting where the contour line crosses the LOP.

Step 808: If more readings are to be taken, the first three steps are repeated.

Step 809: Successive points may be taken, but only the two most recent are shown on the digital map.

Step 810: When done, the user may wish to automatically update his position from the intersection of the two most recent LOPs. If so, Step 811 is performed automatically; otherwise he or she may do it manually, or quit.

Step 811: Current position is updated to be the intersection of the LOPs.

Step 812: Manual position update is achieved when the user moves the cursor to indicate his present position as known from other sources, such as standing at a known crossroad or other marker.

The hand-bearing can also be used to determine a manual fix with only one landmark. A "running-fix" or "advanced LOP" technique uses two or more hand-bearings to the same landmark separated in time. Using DR distance measurement, the earlier azimuth LOPs are shifted perpendicularly along the distances traveled since they were taken. The intersection of these lines with the latest azimuth LOP is the position fix.

This method for determining the location of a user on a digital map using only one landmark includes: a first step of entering positional data relating to a first landmark; a second step of entering a first direction of the first landmark, relative to the user positioned at a preliminary position; a third step of displaying a first LOP on the digital map that indicates a bearing-direction line from the user's preliminary position to the designated landmark, wherein the user's preliminary location on the digital map lies along the first LOP; a fourth step of travelling to a final location and using DR to track the direction and distance travelled from the preliminary location to the final location; a fifth step of entering a direction of the first landmark, relative to the user positioned at the final position; a sixth step of displaying a second LOP on the digital map that indicates a second bearing-direction line from the user's final position to the designated landmark, wherein the user's final position on the digital map lies along the second LOP; a seventh step of shifting both the first LOP and the entered positional data for the first LOP by the direction and distance travelled from the preliminary location to the final location, to thereby effectively transform the first LOP into a new LOP taken from the final position and relating to an effective second landmark; and an eighth step of determining the user's actual position on the digital map to be at an intersection of the new LOP and the second LOP.

2. DR Calibration Using the Digital Map

Calibration of the DR sensors is crucial to accurate DR navigation. The following procedure describes the calibration for both the compass and the ground speed/distance sensor as integrated with the digital mapping system. Refer to flow chart FIG. 9.

Figure 9:
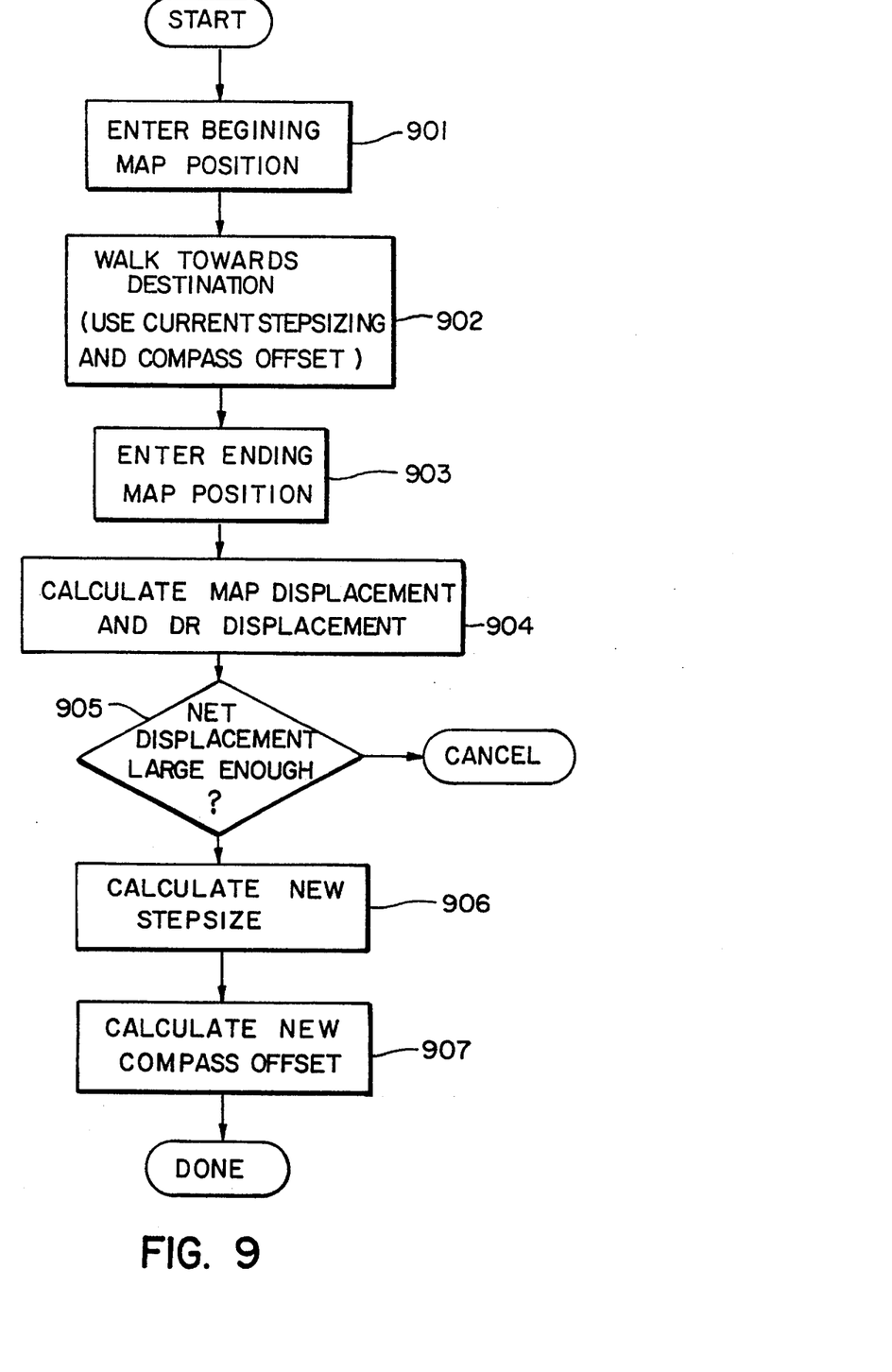
FIG. 9 illustrates the calibration algorithm of the presently preferred embodiment.

Step 901: The user determines his position on the map by reference to local landmarks that are indicated on the map. The user uses the cursor on the display to mark his or her starting position.

Step 902: The user walks at a steady pace to a destination point. The current step size and compass offset are used to calculate a DR path. The path does not have to be straight, since the DR compensates for changes in relative direction.

Step 903: At the ending point, the user again marks his position on the map.

Step 904: Displacement is a vector with North and East components. The map displacement can be determined from the beginning and ending positions on the map. The DR displacement is the calculated North and East components since the beginning of the calibration.

Step 905: Accuracy increases as the beginning and ending points are moved further apart. For example, a circular path has high error. Even thought the total distance may be large, the net displacement is small. A minimum value for net displacement is required to maintain a known accuracy.

Step 906: The new step size is obtained by scaling the old step size by the ratio of the two displacements:

*New step size=Old Step size * (Map Displacement)/(DR Displacement)*

Step 907: The change in the compass offset is the difference between the DR angle and the map angle. The angles are determined from the North and East components of the displacements:

*DR angle=arc tan ((DR East)/(DR North))*

*Map angle=arc tan ((Map East)/(Map North))*

*new offset=old offset+DR angle−Map Angle*

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method of determining displacement of a user on foot, the method comprising the following steps:

generating a set of accelerations corresponding to foot impacts of the user on a surface;

determining a peak acceleration in the set of accelerations;

comparing the peak acceleration to a predetermined minimum threshold value;

comparing, if the peak acceleration is above the predetermined minimum threshold value, a period of time from a previously detected footstep to the determined peak acceleration;

determining whether the period of time is greater than a predetermined minimum threshold period of time;

storing the determined peak acceleration as a detected footstep, if the period of time is determined to be greater than the predetermined minimum threshold period of time; and multiplying stored detected footsteps by a scale factor to thereby determine the displacement of the user on foot.

2. The method of determining displacement of a user on foot according to claim 1, wherein vertical acceleration of the user's body is detected using an accelerometer.

3. A method of determining displacement of a user on foot by detecting a fundamental period of a set of impact accelerations of the user's body, the fundamental period of the set of impact accelerations of the user's body corresponding to a step frequency of the user, the method comprising the following steps:

generating a set of impact accelerations over a period of time related to foot contacts with a ground surface;

obtaining a frequency-domain representation of the set of vertical accelerations;

determining a frequency in the frequency-domain representation that has a largest magnitude of all frequencies in the frequency-domain representation, the frequency in the frequency-domain representation with the largest magnitude being labeled the step frequency of the user on foot; and generating a scale factor to be used in determining the displacement of the user.

4. The method of determining displacement of a user on foot according to claim 3, wherein the generated scale factor is multiplied by a number of footsteps of the user to thereby determine a distance travelled by the user.

5. The method of determining displacement of a user on foot according to claim 4, wherein generated scale factors corresponding to higher step frequencies reflect that footsteps of the user covers more ground on average, and wherein generated scale factors corresponding to lower step frequencies reflect that footsteps of the user cover less ground on average.

6. The method of determining displacement of a user on foot according to claim 3, wherein the generated set of impact accelerations comprises a sliding window of samples.

7. The method of determining displacement of a user on foot according to claim 6, wherein the sliding window of samples comprises $2^N$ samples, where N is an integer, of impact accelerations at any given time.

8. The method of determining displacement of a user on foot according to claim 7, wherein a Fast Fourier Transform (FFT) is performed after every new addition of $2^m$ samples, where m is less than N, of impact accelerations to the sliding window of samples, to thereby generate the frequency-domain representation of the set of impact accelerations.

9. The method of determining displacement of a user on foot according to claim 8, wherein an FFT is not performed on a new $2^m$ samples of impact accelerations if none of the impact accelerations in the new $2^m$ samples exceeds a minimum predetermined threshold.

10. The method of determining displacement of a user on foot according to claim 8, wherein the determined displacement is determined by multiplying:

(a) the scale factor;

(b) the time period corresponding to the $2^m$ vertical acceleration samples; and (c) the generated footstep frequency.

11. The method of determining displacement of a user on foot according to claim 3, wherein a scale factor is not generated if the determined step frequency is outside of a predetermined range of frequencies.

12. The method of determining displacement of a user on foot according to claim 11, wherein the predetermined range of frequencies corresponds to normal walking step frequencies.

13. The method of determining displacement of a user on foot according to claim 12, wherein the predetermined range of frequencies is between 0.5 Hz and 3.0 Hz.

14. In a dead reckoning system that determines a distance travelled by a user on foot by multiplying a number of steps by a step size, a method of dynamically adjusting the step size of the user, the method comprising the following steps:

(a) generating three default values of:
  (1) a default step size S0;
  (2) a default step frequency f0, which is a frequency at which there is no correction to S0; and
  (3) a slope m of a step-size versus step-frequency calibration curve;

(b) detecting a plurality of steps of the user;

(c) noting the time of each of the detected steps;

(d) generating an average step period as an average time between at least two of the plurality of detected steps of the user;

(e) taking a reciprocal of the average step period, to thereby generate a step frequency; and (f) determining a new step size by adding:
  (1) the default step size; and
  (2) a product of both the slope of the step-size versus step-frequency calibration curve and a difference between the default frequency and the generated step frequency.

15. The method of dynamically adjusting the step size of a user according to claim 14, wherein the plurality of steps of the user are detected using a pedometer.

* * * * *